(12) United States Patent
Hunter et al.

(10) Patent No.: US 7,642,096 B2
(45) Date of Patent: Jan. 5, 2010

(54) LIQUID EXPANSION THERMOMETER AND MICROCALORIMETER

(75) Inventors: Ian Warwick Hunter, Lincoln, MA (US); Robert David, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/297,107

(22) Filed: Dec. 8, 2005

(65) Prior Publication Data
US 2006/0133951 A1  Jun. 22, 2006

Related U.S. Application Data

(60) Provisional application No. 60/638,305, filed on Dec. 20, 2004.

(51) Int. Cl.
*G01N 25/20* (2006.01)

(52) U.S. Cl. .................. 436/147; 436/149; 436/150; 436/165; 356/43; 356/44

(58) Field of Classification Search .......... 422/82.05, 422/82.06, 82.09; 436/147, 149, 150, 164, 436/165; 356/43, 44, 450, 451, 453, 454, 356/477
See application file for complete search history.

(56) References Cited

U.S. PATENT DOCUMENTS

| | | | |
|---|---|---|---|
| 4,036,060 A | | 7/1977 | Deficis .................. 73/368 |
| 4,176,552 A | * | 12/1979 | Hammer ............... 374/161 |
| 4,437,761 A | * | 3/1984 | Kroger et al. .......... 356/44 |
| 5,157,457 A | * | 10/1992 | Taylor .................. 356/480 |
| 5,249,865 A | * | 10/1993 | Paranjpe et al. ........ 374/161 |
| 5,413,939 A | * | 5/1995 | Gustafson et al. ...... 436/518 |
| 6,445,453 B1 | * | 9/2002 | Hill ..................... 356/450 |
| 6,455,316 B1 | * | 9/2002 | Turner et al. ............ 436/37 |
| 6,574,490 B2 | * | 6/2003 | Abbink et al. .......... 600/316 |
| 6,716,629 B2 | * | 4/2004 | Hess et al. .............. 435/420 |
| 2003/0095735 A1 | * | 5/2003 | Whateley ............... 385/12 |

FOREIGN PATENT DOCUMENTS

GB   2 040 131   8/1980

OTHER PUBLICATIONS

Batagelj et al., "*Automation of Reading Liquid-in-Glass Thermometers*", IEEE Transactions on Instrumentation and Measurement, vol. 50, No. 6, pp. 1594-1598, Dec. 2001.

(Continued)

*Primary Examiner*—Samuel P Siefke
*Assistant Examiner*—Dwayne K Handy
(74) *Attorney, Agent, or Firm*—Sunstein Kann Murphy & Timbers LLP

(57) ABSTRACT

A calorimeter is provided for measuring a quantity of heat. The calorimeter has a liquid constrained so as to allow expansion of the liquid solely in one dimension along a single axis such that liquid expansion may be measured on the basis of light impinging along the single axis of liquid expansion by means of a non-contact displacement transducer. Interferometric optical means for remote measurement of multiple microcalorimeters permits parallel monitoring of multiple chemical reactions and the performance of parallel biochemical assays.

5 Claims, 5 Drawing Sheets

OTHER PUBLICATIONS

Gao et al., "*Temperature measurement using a gallium-filled carbon nanotube nanothermometer*", Applied Physics Letters, vol. 83, No. 14, pp. 2913-2915, Oct. 2003.

Saarimaa et al., "*Electronic liquid-in-glass thermometer*", Rev. Sci. Instrum., vol. 47, No. 2, pp. 195-197, Feb. 1976.

Schaffer et al., "*Dynamics of Contact Line Pinning in Capillary Rise and Fall*", Physical Review Letters, vol. 80, No. 14, pp. 3069-3072, Apr. 1998.

Stoev et al., "*The effects of thin films on the hydrodynamics near moving contact lines*", Physics of Fluids, vol. 10, No. 8, pp. 1793-1803, Aug. 1998.

Berg et al., "*Measurement of Microkelvin Temperature Differences in a Critical-Point Thermostat*", International Journal of Thermophysics, vol. 19, No. 2, pp. 481-490, 1998.

Cohen et al., "*Viscosity of dilute polyelectrolyte solutions*" J. Chem. Phys., vol. 11, pp. 7111-7116, Jun. 1998.

Velazquez-Campoy et al., "*Development of an isothermal titration microcalorimetric system with digital control and dynamic power Peltier compensation. I. Description and basic performance*", Review of Scientific Instruments, vol. 71, No. 4, pp. 1824-1831, Apr. 2000.

Jacobs et al., "*Measuring Turbidity in a Near-Critical, Liquid-Liquid System: A Precise, Automated Experiment*" International Journal of Thermophysics, Vo. 20, No. 3, pp. 877-887, 1999.

Smith et al., "*Quartz Crystal Thermometer for Measuring Temperature Deviations in the $10^{-3}$ to $10^{-6}$ °C Range*" The Review of Scientific Instruments, vol. 34, No. 3, pp. 268-270, Mar. 1963.

Tilford, C.R., "*Three and a Half Centuries Later- The Modern Art of Liquid-column Manometry*", Metrologia, vol. 94, No. 30, pp. 545-552, 1993.

Hansen et al., "*Comparison of the Detection Limits of Microcalorimeters*" The Thermochemical Institute and the Department of Chemistry, Brigham Young University, May 1983.

Joly et al., "*Thermodilatometric Measurements on Small Samples of Liquid Crystals*", Journal of Thermal Analysis, vol. 37, pp. 2483-2495, 1991.

\* cited by examiner

LIQUID EXPANSION THERMOMETER AND MICROCALORIMETER

The present application claims priority from U.S. Provisional Patent Application Ser. No. 60/638,305, filed Dec. 20, 2004, and incorporated herein by reference.

TECHNICAL FIELD

The present invention relates to a device and method for optical measurement of heat change as a result of a chemical reaction, and, more particularly, for parallel measurement of multiple reactions by interferometric measurement of liquid expansion.

BACKGROUND OF THE INVENTION

The dominant existing methods for high-throughput drug discovery currently involve fluorescent or radioactive labeling of a target molecule. This is disadvantageous in that a new assay must be designed for each target molecule, a costly and time-consuming process. Moreover, the label may interfere with the natural biological activity of the target molecule. Current techniques are discussed by Macarrón et al., "Design and implementation of high-throughput screening assays," in Janzen, ed., *High Throughput Screening: Methods and Protocols*, (2002), which is incorporated herein by reference.

Thermodynamic indicators of reaction progress in microsamples would obviate the development of specific labels, however existing microcalorimeters lack the resolution and/or throughput (i.e., adaptability to parallel measurement) needed for high throughput drug discovery.

Several types of thermometers with microkelvin-level resolution at room temperature have been reported in the literature. Smith et al., *Quartz crystal thermometer for measuring temperature deviations in the $10^{-3}$ to $10^{-6\circ}$ C. range*, Rev. Sci. Instrum., vol. 34, pp. 268-70 (1963) describe a quartz resonator with a measured noise level of 4 μK. A thermistor with sub-microkelvin noise is mentioned in Hansen et al., *Comparison of the detection limits of microcalorimeters*, Thermochim. Acta, vol. 70 pp. 257-268 (1983). Similar thermostats have been used to measure the properties of liquids near their critical points, as described, for example by Cohen et al., *Viscosity of dilute poly-electrolyte solutions*, J. Chem. Phys., vol. 88, pp. 7111-16, (1988). Finally, thermopiles may be used to measure small temperature differences such as in the thermopile microcalorimeter described by Velázquez-Campoy et al., *Development of an isothermal titration microcalorimetric system with digital control and dynamic power Peltier compensation. I. Description and basic performance*, Rev. Sci. Instrum., vol. 71, pp. 1824-31 (2000).

Interferometry has been used to measure the expansion of solids and liquid crystals, such as by Joly et al., *Thermodilatometric measurements on small samples of liquid crystals*, J. Therm. Anal., vol. 37, pp. 2483-95 (1991), incorporated herein by reference. Instrumental use of interferometry to record meniscus levels has been limited to manometers where such techniques were possible by virtue of the large meniscus cross-section, but were found to be limited in resolution due to vibration problems, as discussed by Tilford, *Three and a halfcenturies later—the modern art of liquid-column manometry*, Metrologia, vol. 30, 545-52 (1994), incorporated herein by reference.

SUMMARY OF THE INVENTION

In accordance with preferred embodiments of the present invention, a calorimeter is provided for measuring a quantity of heat. The calorimeter has a liquid constrained so as to allow expansion of the liquid solely in one dimension along a single axis such that liquid expansion may be measured on the basis of light impinging along the single axis of liquid expansion.

In accordance with further embodiments of the invention, the calorimeter may also have a non-contact displacement transducer that may include an optical surface displacement sensor and, more specifically, an interferometric sensing arrangement such as a Michelson interferometer or a Mach-Zehnder interferometer. The liquid expansion may also be measured confocally. The calorimeter may also have a test capillary whereby expansion of the liquid is constrained to one dimension.

In accordance with yet further embodiments of the invention, the calorimeter may also have a control capillary, wherein the differential liquid expansion between liquid in the test capillary and liquid in the control capillary is measured interferometrically in a Mach-Zehnder configuration or a Michelson configuration.

In other embodiments of the invention, a liquid expansion thermometer is provided that has a liquid constrained so as to allow expansion of the liquid in only a single expansion dimension and an interferometer for measuring displacement of a surface of the liquid in the expansion dimension. The liquid may be aqueous. A second liquid, immiscible in the first liquid, may be present, wherein the first and second liquid share an interface.

Another aspect of the invention is a system for monitoring a plurality of chemical reactions disposed in an array configuration of liquid samples. The system has a plurality of liquid expansion calorimeters, one liquid expansion calorimeter associated with each chemical reaction of the array.

In accordance with yet another aspect of the invention, a monitoring system is provided for monitoring a plurality of chemical reactions. The monitoring system has an array of discrete reaction loci and at least one interferometer for remotely measuring a thermodynamic variable of each sample.

In other embodiments of the invention, a method is provided for monitoring heat evolved in a chemical reaction that has steps of:
  a. providing a liquid expansion calorimeter;
  b. conducting heat from the chemical reaction to the liquid expansion calorimeter; and
  c. monitoring a change in heat content of the liquid expansion calorimeter.

In another embodiment of the invention, a thermodynamic variable associated with a reaction may be measured by mixing two reactants on the surface of a liquid expansion calorimeter. And, in yet another embodiment of the invention, two or more reactants may be mixed to constitute the expansion liquid of a liquid expansion calorimeter.

BRIEF DESCRIPTION OF THE DRAWINGS

The invention will more readily be understood by reference to the following description taken with the accompanying drawings in which.

DETAILED DESCRIPTION OF PREFERRED EMBODIMENTS

Figure 1:
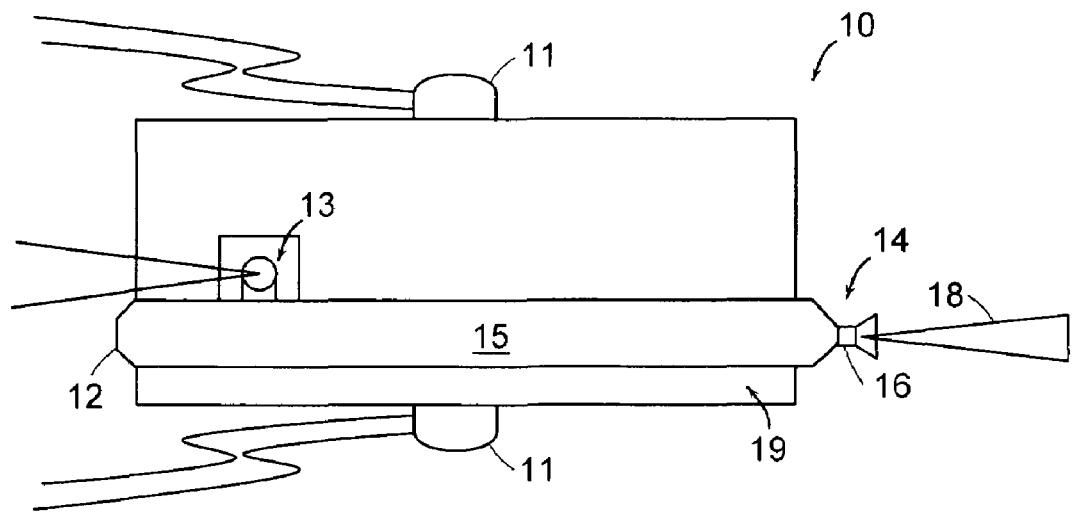
FIG. 1 depicts a liquid-filled capillary calorimeter, mounted for interferometric interrogation in accordance with the present invention, with coupled RTDs for purposes of calibration.

The term "calorimeter," shall refer herein to an instrument employed for the measurement of the extrinsic quantity of heat, or changes in the quantity of heat or other extrinsic thermodynamic quantities such as enthalpy, in any case measured in units of energy such as joules, ergs, calories, etc., unless the context dictates otherwise.

The term "thermometer," shall refer herein to an instrument employed for the measurement of the intrinsic quantity of temperature, measured in units of kelvins, etc., unless the context dictates otherwise.

It is to be understood that when aspects of the invention are described with respect to either a calorimeter or a thermometer, their application to the other context is to be understood, unless the context dictates otherwise.

In accordance with certain embodiments of the present invention, the meniscus level within a liquid-in-glass thermometer is monitored by an interferometer, allowing temperature changes of below 2 μK to be resolved. This high resolution may be used advantageously in critical point studies, for example, and, when configured for calorimetry, the techniques of the present invention allow the sample itself to be used as the thermometric liquid, thereby minimizing heat loss.

The resolution of mercury thermometers is limited by imperfections in the bore, which cause the meniscus to move in small jumps. This effect was not noticeable in our measurements. In the last section, we will suggest an explanation for why this was. In other research in liquid expansion thermometry, a capacitive sensor has been used to read the meniscus level in a mercury thermometer with 0.3 mK resolution. More recent developments, which include automated reading of meniscus level, as described by Batagelj et al., Automation of reading liquid-in-glass thermometers, *IEEE Trans. Instrum. Meas.* 50, pp. 1594-98 (2001), incorporated by reference, and a tiny thermometer with a carbon nanotube for its bore, have not focused on improving resolution.

A thermometer, in accordance with one embodiment of the invention, is now described with reference to FIG. 1. The thermometer, designated generally by numeral 10, consists of a capillary 12, with typical dimensions of 23 mm length of 0.75 mm ID and borosilicate glass composition (as provided by Friedrich & Dimmock), however any lengths and diameters are within the scope of the present invention. A neck 14, which formed the thermometer bore, was drawn at the top of the capillary using a laser-based pipette puller (Sutter P-2000). The capillary was then filled with 10 μL of distilled water 15 and the bottom sealed using the fine flame of a hydrogen torch (Arizona Hydrogen Hydroflame III). The use of other liquids is also encompassed within the scope of the present invention. A thin layer of mineral oil 16 (supplied by Alfa Aesar) is added above the water to prevent evaporation.

The top surface of oil 16 (the meniscus), about 0.1 mm in diameter, is used as the reflecting surface for the interferometer beam 18 (FIG. 1). Attention is preferably paid not to expose the capillaries for long to the open air before filling, but the scope of the invention does not impose requirements of cleaning procedures or applied coatings.

A Michelson interferometric arrangement for interrogating the surface displacement of the liquid meniscus is now described with reference to FIG. 2. It is to be understood that other interferometric arrangements, indeed, other methods of remotely interrogating the displacement of the liquid meniscus from a direction parallel to the direction of liquid expansion, are within the scope of the present invention. These methods may include confocal measurement of the displacement of the liquid surface. A light source 20 for the Michelson interferometer may include, by way of example, a 656 nm fiber-coupled diode laser. The object arm 24 and reference arm 22 of the interferometer may each be on the order of 100 mm long, and 90° apart, with a mirror 25 as the reference surface. A 0.14 NA long-working-distance objective 26 focuses the object beam on the meniscus 27. The interfering beams are detected at detector 28 which may be an avalanche photodiode (APD). The current output of the APD is converted to a voltage and low-pass filtered at 0.3 Hz by a current amplifier 29.

Thermometer 10 is preferably isolated from ambient temperature fluctuation. To that end, an enclosure, typically about 0.9 m×0.6 m×0.6 m, and made of double layers of 50 mm thick vacuum insulation panels, may be employed. The capillary, optics, and photodiode are located inside, on top of a large plastic heat sink. The capillary itself is mounted inside an additional aluminum heat sink 19 (shown in FIG. 1). Temperature controllers limited temperature drift at the capillary to roughly 1 mK per hour, about a set point of approximately 27° C. The laser and electronics are preferably maintained outside the enclosure, with the laser fiber optic and other wires running through a small opening in one of the enclosure walls. Other temperature controllers are preferably mounted on the laser exterior to stabilize its output power.

Meniscus displacement was calibrated to temperature change by allowing the capillary temperature to drift in one direction, and comparing the readings of nearby resistance temperature detectors (RTDs) 11 with the number of fringes crossed by the interferometer signal. In one embodiment of the invention, the RTD resolution is about 0.5 mK. While evaporation may cause a steady drop in the meniscus level while the RTD readings is constant, by measuring the rate of evaporation, the total evaporation during calibration may be subtracted to get a correct result.

A resistor 13 mounted on the capillary with thermal grease served as a heater for determining the temperature resolution of the thermometer. Heat was applied while the interferometer signal was in the linear, sensitive part of the sine wave (away from the peaks).

In accordance with preferred embodiments of the invention, data collection, temperature control, and heat application are under computer control. The enclosure may also be rested on a vibration isolation table.

Figure 3:
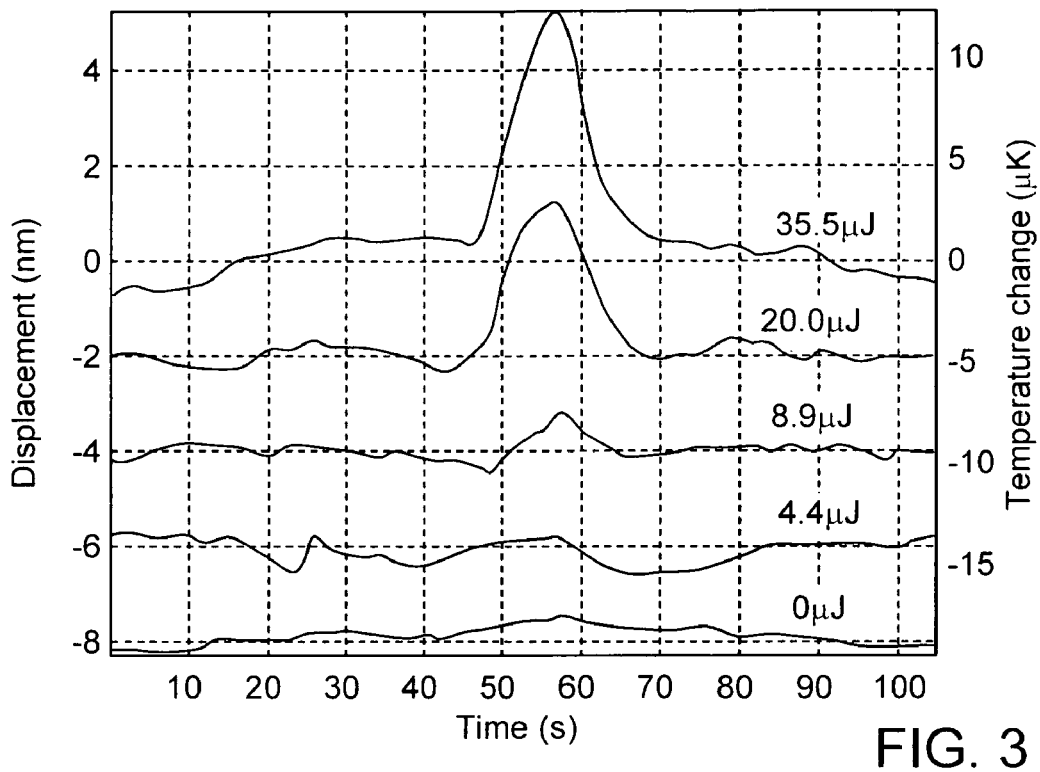
FIG. 3 plots time histories of displacement of the meniscus of the capillary calorimeter of FIG. 1, plotted for 5 different quantities of heat released by a calibrating resistor during the time interval between 46 and 56 seconds.

Calibration values were in the range expected from thermal expansion and the geometry (about 0.4 mm/K). Typical results for the thermometer resolution are shown in FIG. 3. The total deviation of the control signal over 105 s was below ±1.5 µK, and may be further reduced by use of shorter capillaries that admit the laser beam without passing through the glass side walls. The values given are the average temperature change of all the water in the capillary, even though, in the experimental configuration employed for demonstration of the invention, only a portion of the water was substantially heated by the resistor.

Figure 4:
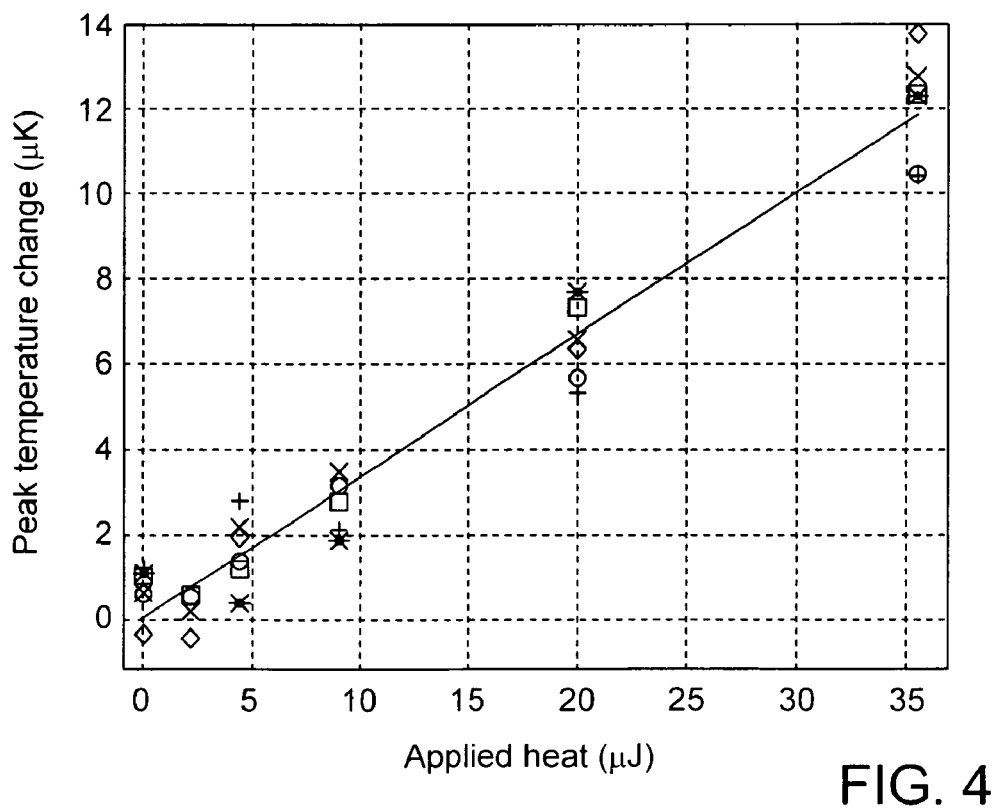
FIG. 4 plots the peak temperature change after the heat, plotted on the abscissa, has been applied to the calorimeter of FIG. 1.

FIG. 4 is illustrative of the reproducibility of the results. Noise was measured to be about half as large when the capillary was replaced with a mirror.

Larger temperature changes are measured by fringe counting, with a resolution of 0.5 mK or better. The maximum range was found, in one embodiment, to be about 0.2 K, limited by the meniscus moving out of focus. The usable lifetime of each capillary has been determined to be at least a few weeks.

The noise level observed in one embodiment of the invention was similar whether the meniscus was rising or falling, and independent of its speed. It has been suggested elsewhere that contact angle hysteresis can be mitigated by the formation of a wetting film above the meniscus, provided the meniscus motion is slow enough that the fluid molecules in the film have time to self-arrange. See, for example, Schäffer et al., *Dynamics of contact line pinning in capillary rise and fall*, Phys. Rev. Lett., vol. 80, 3069-72 (1998), incorporated herein by reference. Our observations support this hypothesis; and, in fact, a permanent oil film did appear to line the capillary walls above the menisci in our capillaries. No such film would be present in a mercury thermometer.

Figure 2:
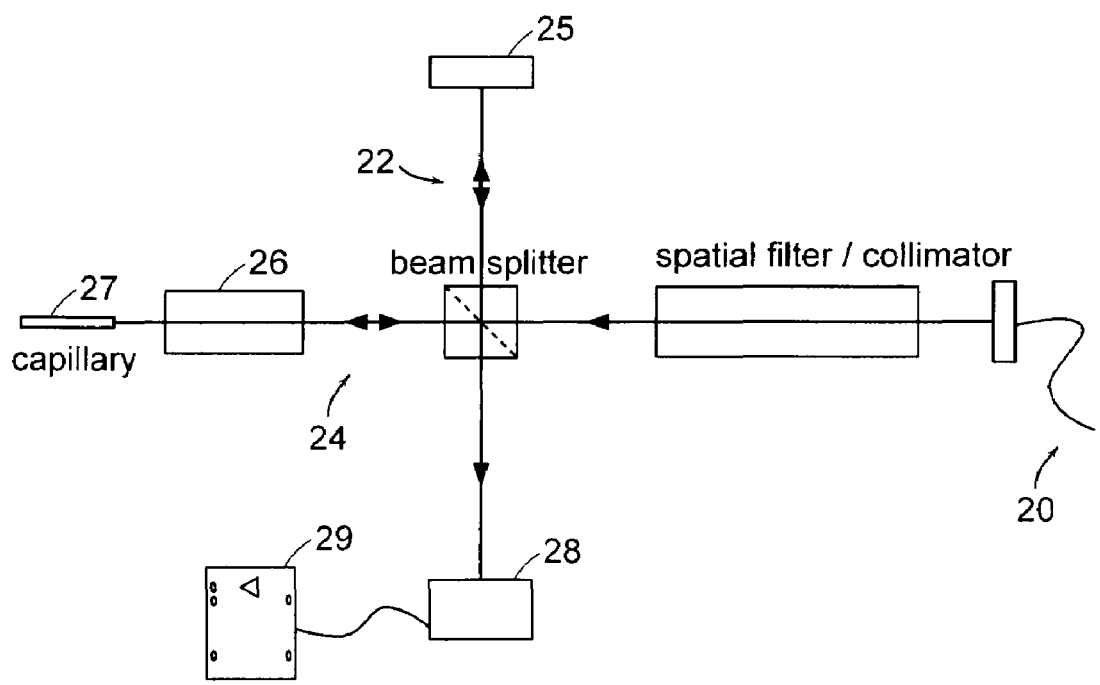
FIG. 2 is a schematic layout of a Michelson interferometric probe for interrogating the expansion of the liquid within the capillary calorimeter of FIG. 1.

In accordance with alternate embodiments of the present invention, a control capillary may be added to the instrument, in reference arm 22 of the Michelson interferometer embodiment shown in FIG. 2, for example, to reduce common mode noise, relax the temperature control requirements, and shorten the long equilibration time required before each experiment. Other interferometric configurations such as Mach Zehnder configurations are also within the scope of the invention and may, similarly, contain test and reference capillaries.

Figure 7:
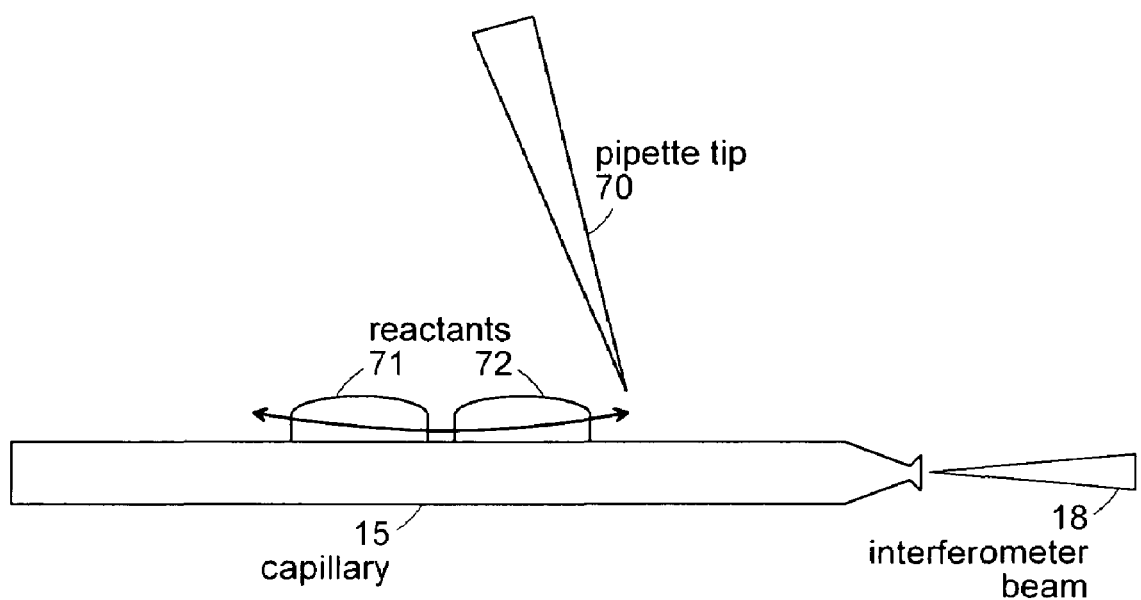
FIG. 7 depicts calorimetry of a chemical reaction initiated by combining reactants, in accordance with an embodiment of the present invention.

Referring now to FIG. 7, a microcalorimeter may also be realized by mixing two drops 71 and 72 of reactants placed on top of the capillary. This may be done by drawing a pipette tip 70 through the two drops to merge them on command. Each drop has a volume of 2 µL, though the practice of the invention with respect to droplets of any size is within the scope of the present invention. The environment around capillary 15 is preferably humidified in order to avoid evaporation of the liquid in the drops.

Moreover, two or more reactants may be mixed and the resultant mixture may itself constitute the expansion liquid of the liquid expansion calorimeter.

Figure 5:
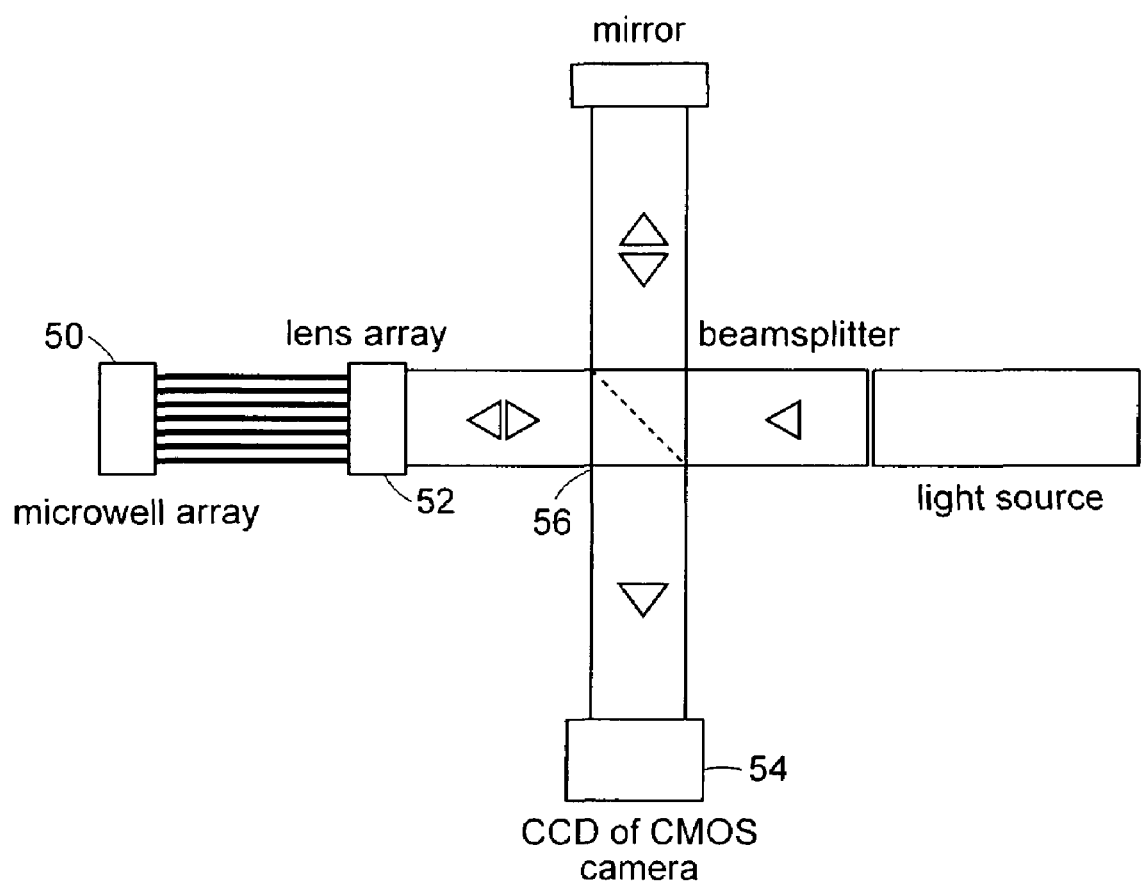
FIG. 5 is a schematic depiction of one embodiment of the invention in which heat change in an array of microwells is probed in parallel by means of a Michelson interferometric arrangement.

A thermometer may also be transformed into a microcalorimeter that measures heat changes resulting from chemical reactions taking place inside the capillary. The optical nature of the technique may advantageously allow application of high-throughput parallel techniques. One such technique is shown in FIG. 5, where an array of microwells 50 is illuminated, via a lens array 52, and reflections from liquid in individual wells are imaged, as combined, by beamsplitter 56, with a reference image, so as to interfere at the focal plane of a CCD or CMOS camera 54.

Figure 6:
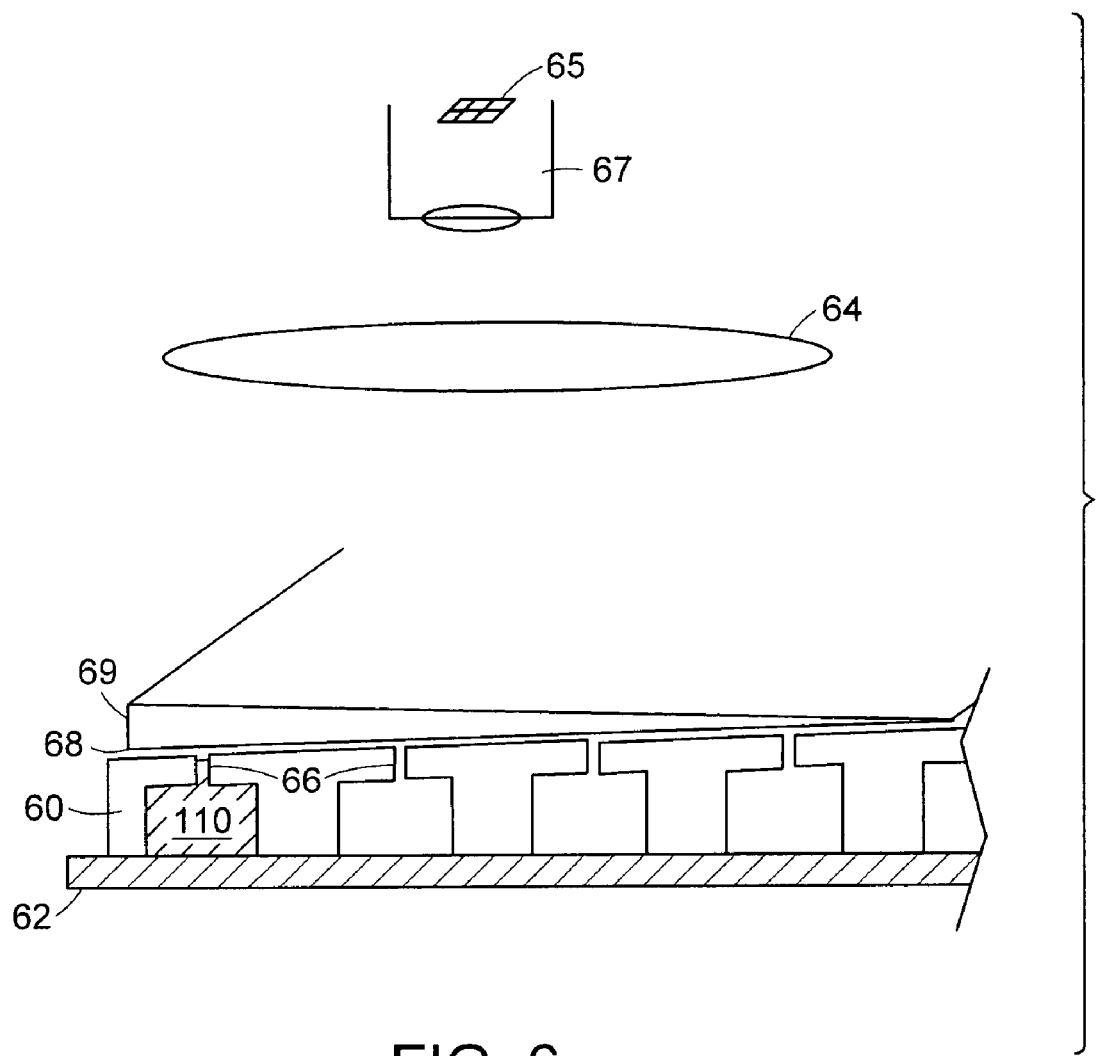
FIG. 6 is a schematic depiction of another embodiment of the invention in which heat change in an array of microwells is probed interferometrically in parallel.

Another embodiment is described with reference to FIG. 6. In FIG. 6, a microwell array 60 is shown as filled with a plurality of liquid samples 110. After filling, the larger-area side of each well is closed by means of a cover plate 62. Each microwell has a narrow capillary segment 66 into which the liquid sample rises, expanding if the heat content of the sample increases. The level of the meniscus of each sample may be monitored remotely by imaging each of the capillary ends, by means of the transfer optics denoted schematically as element 64, onto focal plane array 65 in video camera 67. Optical surface 68 of transparent wedge 69 forms an etalon with each of the discrete menisci, so that interference fringes may be measured and counted in parallel, if the array is illuminated from above in monochromatic light. Optical surface 68 may be coated to increase the finesse of the etalon formed by each meniscus and optical surface 68. Wedge 69 is provided so as not to blur interference fringes by multiple etaloning due to parallel surfaces.

The described embodiments of the invention are intended to be merely exemplary and numerous variations and modifications will be apparent to those skilled in the art. All such variations and modifications are intended to be within the scope of the present invention as described herein and as defined in any appended claims.

We claim:

1. A method for monitoring heat evolved in a chemical reaction, the method comprising:
   a. constraining a liquid in a capillary providing a liquid expansion calorimeter, having a liquid therein;
   b. conducting heat from the chemical reaction to the liquid expansion calorimeter; and
   c. interferometrically measuring the displacement of a surface of the liquid in the capillary and inferring therefrom the heat evolved in the chemical reaction.

2. A method in accordance with claim 1, wherein the chemical reaction is initiated by combining two reactants on the liquid expansion calorimeter.

3. A method in accordance with claim 1, wherein a combination of the two reactants comprises an expansion liquid of the liquid expansion calorimeter.

4. A method for monitoring an array of parallel biochemical assays, the method comprising:
   a. constraining a liquid associated with each biochemical assay within a volume including a capillary segment,
   b. interferometrically measuring a change in optical pathlength to a surface of the liquid; and
   c. correlating the change in optical pathlength to the surface of the liquid with a thermodynamic variable selected from the group of heat, temperature, volume, and pressure.

5. A method in accordance with claim 4, wherein the parallel biochemical assays are conducted within an array of microwells.

* * * * *